US009533933B2

(12) United States Patent
Micoine et al.

(10) Patent No.: US 9,533,933 B2
(45) Date of Patent: Jan. 3, 2017

(54) PROCESS FOR PREPARING CYCLODODECANONE

(71) Applicants: Kevin Micoine, Herten (DE); Ralf Meier, Dortmund, DE (US); Juergen Herwig, Huenxe (DE); Martin Roos, Haltern am See (DE); Harald Haeger, Luedinghausen (DE); Luca Cameretti, Dortmund (DE); Jens Doering, Dortmund (DE)

(72) Inventors: Kevin Micoine, Herten (DE); Ralf Meier, Dortmund, DE (US); Juergen Herwig, Huenxe (DE); Martin Roos, Haltern am See (DE); Harald Haeger, Luedinghausen (DE); Luca Cameretti, Dortmund (DE); Jens Doering, Dortmund (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/815,014

(22) Filed: Jul. 31, 2015

(65) Prior Publication Data
US 2016/0031784 A1 Feb. 4, 2016

(30) Foreign Application Priority Data

Aug. 1, 2014 (EP) .................... 14179454

(51) Int. Cl.
| C07C 45/51 | (2006.01) |
| C07C 45/58 | (2006.01) |
| C07D 201/04 | (2006.01) |
| B01J 23/44 | (2006.01) |
| C07C 45/82 | (2006.01) |
| C07C 249/04 | (2006.01) |
| C07D 225/02 | (2006.01) |
| C07D 301/12 | (2006.01) |
| C08G 69/16 | (2006.01) |
| C07C 29/52 | (2006.01) |
| C07C 45/00 | (2006.01) |
| C07C 45/28 | (2006.01) |
| C07C 49/413 | (2006.01) |

(52) U.S. Cl.
CPC .............. *C07C 45/512* (2013.01); *B01J 23/44* (2013.01); *C07C 29/52* (2013.01); *C07C 45/002* (2013.01); *C07C 45/28* (2013.01); *C07C 45/58* (2013.01); *C07C 45/82* (2013.01); *C07C 249/04* (2013.01); *C07D 201/04* (2013.01); *C07D 225/02* (2013.01); *C07D 301/12* (2013.01); *C08G 69/16* (2013.01); *C07C 49/413* (2013.01)

(58) Field of Classification Search
CPC ... C07C 249/04; C07C 49/413; C07D 201/04; C08G 69/16
See application file for complete search history.

(56) References Cited

U.S. PATENT DOCUMENTS

| 3,173,964 | A | * | 3/1965 | Perry, Jr. ............... C07C 5/05 562/543 |
| 3,708,506 | A | * | 1/1973 | Brunie ................ C07D 303/04 549/530 |
| 6,204,416 | B1 | * | 3/2001 | Liedloff ................ C07C 45/58 568/338 |
| 6,515,185 | B1 | * | 2/2003 | Kuroda ................ C07C 29/132 568/338 |
| 7,253,329 | B2 | | 8/2007 | Herwig et al. |
| 9,000,223 | B2 | * | 4/2015 | Micoine ................ B01J 23/38 568/341 |
| 2003/0139596 | A1 | * | 7/2003 | Kuroda ................ C07D 201/06 540/464 |
| 2004/0116722 | A1 | | 6/2004 | Herwig et al. |

FOREIGN PATENT DOCUMENTS

| EP | 1 090 900 A1 | 4/2001 |
| EP | 1 329 448 A1 | 7/2003 |
| EP | 1 411 050 A1 | 4/2004 |
| JP | 56110680 A | 9/1981 |
| JP | 2000319219 A | 11/2000 |
| JP | 2001172211 A | 6/2001 |
| JP | 2004099585 A | 4/2004 |
| JP | 2004131505 A | 4/2004 |

OTHER PUBLICATIONS

U.S. Appl. No. 14/815,014, filed Jul. 31, 2015, Micoine, et al.
U.S. Appl. No. 14/714,985, filed May 18, 2015, Meier, et al.
U.S. Appl. No. 14/814,984, filed Jul. 31, 2015, Micoine et al.
Thomas Schiffer, et al., "Cyclododecanol, Cyclododecanone, and Laurolactam" Ullmann's Encyclopedia of Industrial Chemistry, XP002734395, Jun. 15, 2000, 5 Pages.

* cited by examiner

Primary Examiner — Gregory Listvoyb
(74) Attorney, Agent, or Firm — Oblon, McClelland, Maier & Neustadt, L.L.P.

(57) ABSTRACT

Cyclododecanone (CDON) is prepared by epoxidizing cyclododecene (CDEN) to epoxycyclododecane (CDAN epoxide), and rearranging the CDAN epoxide to CDON to obtain a mixture comprising said CDON and CDEN, wherein CDEN is separated from the CDON-containing mixture and sent to the epoxidation to CDAN epoxide in step a.

13 Claims, 1 Drawing Sheet

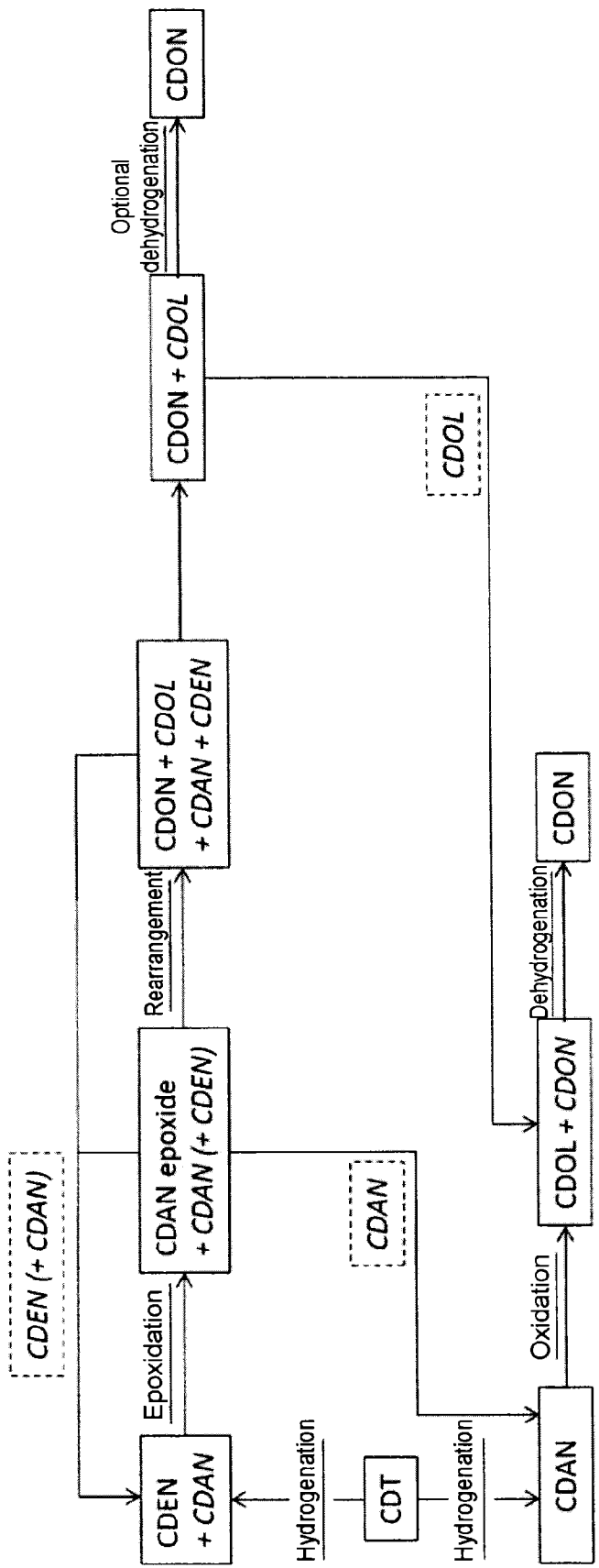

PROCESS FOR PREPARING CYCLODODECANONE

BACKGROUND OF THE INVENTION

Field of the Invention

The present invention relates to a process for preparing cyclododecanone, to a process for preparing laurolactam and to a process for preparing nylon-12.

Discussion of the Background

Cyclododecanone (CDON) is used for the synthesis of laurolactam. The lactam in turn is suitable for the preparation of nylon-12.

The preparation of CDON may proceed from cyclododecatriene (CDT). First of all, a selective hydrogenation of cyclododecatriene (CDT) to cyclododecene (CDEN) may be undertaken. This is followed by an epoxidation of CDEN to epoxycyclododecane (CDAN epoxide) and the rearrangement of CDAN epoxide to cyclododecanone (CDON). Proceeding from CDEN, the CDON synthesis comprises the following steps:

a. epoxidizing cyclododecene (CDEN) to epoxycyclododecane (CDAN epoxide) and
b. rearranging the CDAN epoxide to CDON to obtain a mixture comprising CDEN.

The mixture (CDON-containing mixture) which is obtained from the rearrangement thus comprises at least CDON and CDEN.

In this process for preparing CDON, the problem occurs that significant amounts of CDEN can arise. This problem is aggravated by the ageing of catalysts which may be used. The amount of CDEN obtained may be more than 5 by weight, based on the resulting CDON-containing mixture from the rearrangement.

The high proportion of CDEN may have adverse effects on the downstream reactions such as the preparation of laurolactam. In addition, small product yields are comparatively uneconomic.

SUMMARY OF THE INVENTION

In this respect, the problem addressed by the present invention was that of providing a novel process for preparing CDON which reduces the proportion of CDEN in the CDON end product and increases the yield of CDON. In addition, the preparation process was to appear more economically viable overall.

The present invention encompasses in one embodiment a process for preparing cyclododecanone (CDON) by a reaction route I, said reaction route I comprising:

a. epoxidizing cyclododecene (CDEN) to epoxycyclododecane (CDAN epoxide), and
b. rearranging the CDAN epoxide to CDON to obtain a mixture comprising said CDON and CDEN, wherein CDEN is separated from the CDON-containing mixture and sent to the epoxidation to CDAN epoxide in step a.

In another embodiment, the present invention relates to a process for synthesizing laurolactam from CDON, wherein the CDON is prepared as above.

In yet another embodiment, the present invention relates to a process for preparing nylon-12 from CDON, wherein the CDON is prepared as above.

BRIEF DESCRIPTION OF THE DRAWING

FIG. 1 shows a flow diagram with the corresponding reactions. The compounds in italics are by-products of each reaction.

DETAILED DESCRIPTION OF THE INVENTION

All ranges described hereinafter include all values and subvalues between the lower and higher limits of the given ranges.

A novel process for preparing CDON by a reaction route I has been found, said route I comprising a. epoxidizing cyclododecene (CDEN) to epoxycyclododecane (CDAN epoxide), and
b. rearranging the CDAN epoxide to CDON to obtain a mixture comprising said CDON and CDEN, wherein CDEN is separated from the CDON-containing mixture and sent to the epoxidation to CDAN epoxide in step a.

The CDON process of the invention can be conducted continuously or batchwise.

The rearrangement is preferably conducted at a maximum hydrogen pressure of 0.9 bar. Preferably, the hydrogen pressure is 0 to 0.9 bar, more preferably 0 to 0.5 bar. The process according to the invention can be conducted without hydrogen, but it is preferable to initially charge at least a small hydrogen content to prevent unsaturated by-products. This hydrogen content may be 0.05 to 0.5 bar, preferably 0.1 to 0.4 bar.

The pressure figures given above relate to the partial pressure of hydrogen in the system. Typically, components of the reaction mixture including the solvent, air or inert gases such as nitrogen or argon are further gaseous constituents of the system.

A rearrangement in the context of the CDON process of the invention is especially understood to mean a reaction in which at least 90% by weight of CDON, based on the total weight of CDON and CDOL formed, is obtained.

Preferably, the CDEN for the epoxidation (step a) is obtained from CDT. The CDT in turn can be obtained from 1,3-butadiene. The selective hydrogenation of CDT can be effected in the gas phase with a low partial pressure of hydrogen and a Pd-containing catalyst (EP 1457476). The step typically gives rise to 5% to 15% by weight of CDAN (cyclododecane) in CDEN.

The epoxidation of CDEN as per step a can be conducted with hydrogen peroxide, by means of a phase transfer catalyst and a metal salt at acidic pH. The CDAN present in the CDEN acts as a phase separation accelerator (EP 1411050, EP 1411051). After the reaction, CDAN epoxide is obtained, which may further comprise CDAN, unreacted CDEN or both.

CDEN, which has not been converted to CDAN epoxide (unreacted CDEN) can be at least partly removed prior to the rearrangement (step b).

The CDAN present after the epoxidation should be at least partly removed, in order that CDAN does not become concentrated as a result of the circulation. Preferably, at least 50% by weight of the CDAN, based on the total weight of CDAN, preferably 90% by weight, more preferably 95% by weight, even more preferably 98% by weight and especially 100% by weight is removed. The proportion of CDAN to be removed, especially in the cases where little or no CDEN is present, may be at least 90% by weight. Little CDEN is present when the proportion of CDEN in the mixture of CDAN epoxide, CDAN and CDEN is less than 5% by weight.

If unreacted CDEN is present after the epoxidation, CDEN can be fed as a mixture with CDAN at least partly back to the epoxidation or, without removal, to the rearrangement (step b). The CDAN removed can then be oxidized to CDON, in which case CDOL may be formed at least partly. The CDOL can then be dehydrogenated to CDON.

The rearrangement as per step b is preferably effected in the presence of a noble metal catalyst (catalyst system), the catalyst preferably comprising titanium dioxide, zirconium dioxide or both. This reaction step forms CDON, which may additionally contain CDAN, CDEN, CDOL or mixtures thereof as by-products (CDON-containing mixture). Further by-products having a higher boiling point than CDON may likewise be present (high boilers). Preferably, the rearrangement is not conducted in the presence of alkali metal hydroxides as catalyst.

The noble metal in the catalyst system is preferably selected from ruthenium, rhodium, palladium, osmium, iridium and platinum, preference being given to ruthenium, palladium and platinum, and particular preference to palladium. The noble metal may be in the form of powder (unsupported) or in supported form. Elemental noble metals or oxides thereof, for example, are suitable in powder form.

In addition, at least one metal oxide may be present as a further constituent of the catalyst system. The metal oxide in the catalyst system comprises titanium dioxide, zirconium dioxide or mixtures thereof, or consists of at least one of the aforementioned oxides. These also include titanium dioxide- or zirconium dioxide-doped or -coated substances such as alumina or silica.

The metal oxide in the catalyst system may function as a support for the noble metal in the catalyst system. The noble metal may optionally be applied to an alternative support selected, for example, from alumina, silica or activated carbon. Titanium dioxide or zirconium dioxide are preferred supports.

The metal oxides in the catalyst system and the alternative supports may be in the form of powders or shaped bodies. Suitable shaped bodies are spheres, extrudates, tablets, granules and pellets. It is preferable that the supports of the noble metal are in the form of shaped bodies. It is likewise preferable that the metal oxide in the catalyst system, if it does not function as a support, is in the form of shaped bodies.

The catalyst system may consequently independently be present as one of the following system forms:
  I) the noble metal is unsupported; the metal oxide present in the catalyst system is at least titanium dioxide or zirconium dioxide;
  II) the noble metal is supported, where the support does not comprise or consist of titanium dioxide and/or zirconium dioxide. The system additionally comprises at least one metal oxide selected from titanium dioxide and zirconium dioxide.
  III) The noble metal is supported on a metal oxide selected from titanium dioxide and zirconium dioxide, preferably with no titanium dioxide present.

System forms II and III are preferred, system form III being particularly preferred.

Suitable titanium dioxide as a metal oxide in the catalyst system can be obtained by the sulphate process, the chloride process, or by flame hydrolysis (pyrogenic process) of titanium tetrachloride. All the processes are known to those skilled in the art. Suitable polymorphs are rutile and anatase, and the titanium dioxide used may comprise mixtures of the polymorphs mentioned.

The titanium dioxide prepared by the sulphate or chloride process may give an acidic reaction in water, the compounds typically having a pH of 3 or less (acidic titanium dioxide). Acidic titanium dioxide likewise usually contains more than 5% by weight, based on the total weight of the titanium dioxide support, of substances such as titanyl sulphate or titanyl hydroxide. A titanium dioxide based on an acidic titanium dioxide is commercially available as Aerolyst 7750 (Evonik, Germany). Acidic titanium oxide is less preferred for the present process. In other words, it is preferable not to use acidic titanium dioxide. Suitable nonacidic titanium dioxide, which is preferred, exhibits a pH of 5 or more in water.

Particularly preferred titanium dioxide is obtained by means of flame pyrolysis, as described, for example, in DE-A-830786.

Suitable titanium dioxide is obtainable under the Aeroxide P25 titanium dioxide (powder) or Aerolyst 7711 (shaped bodies) name from Evonik, Germany, and Hombikat M234 (shaped bodies) from Sachtleben, Germany.

Zirconium dioxide (zirconium(IV) oxide) is obtainable, for example, from zirconium hydroxide, by calcining it at more than 200° C., for example at 350° C. The zirconium dioxide may be doped, for example, with yttrium oxide.

Suitable zirconium dioxide is monoclinic or tetragonal. Mixtures of these polymorphs are possible.

The metal oxide in the catalyst system may have an average bulk density of 0.5 to 2 $g/cm^3$.

The metal oxide in the catalyst system may have a BET surface area of at least 5 $m^2/g$.

The proportion of noble metal, based on the total weight of noble metal and support, may be 0.01% to 5% by weight, preferably 0.05% to 1.2% by weight and more preferably 0.1% to 0.6% by weight.

The noble metal may be distributed on or within the support.

The molar proportion of noble metal, based on the molar amount of CDAN epoxide may be 0.00001 to 0.1, preferably 0.0001 to 0.01.

The molar proportion of metal oxide in the catalyst system, based on the molar amount of the epoxycyclododecane, may be 0.01 to 100, preferably 0.01 to 10.

The CDEN is removed from the reaction mixture and sent to the epoxidation. If CDAN is present, it is typically sent to the epoxidation as a mixture with CDEN.

The remaining mixture comprising CDON and high boilers including CDOL can be hydrogenated in the presence of hydrogen and a catalyst in order to remove the unsaturated by-products. Subsequently, the pure CDON product is separated from a high boiler fraction including CDOL by distillation, for example.

CDOL can subsequently be distilled out of this high boiler fraction, and CDOL can be converted to CDON within reaction route I by means of a dehydrogenation catalyst. However, it is preferable to send the CDOL removed, prior to the dehydrogenation, to a reaction route II for preparation of CDON.

Reaction route II comprises the following steps:
  a. hydrogenation of CDT to CDAN,
  b. oxidation of CDAN to give a mixture comprising CDOL and CDON and
  c. dehydrogenation of CDOL to CDON.

Suitable catalysts for the dehydrogenation of CDOL contain copper or copper compounds, for example copper(II) oxide.

The CDOL from route I is preferably fed in prior to step c of route II, the dehydrogenation.

The CDAN removed from route I can likewise be fed to reaction route II prior to performance of the oxidation. The CDAN here is preferably fed in prior to step b of route II, the oxidation. The CDAN can be removed, for example, after the epoxidation of route I.

In this respect, reaction routes I and II can be combined in such a way that CDAN or CDOL obtained are separated and removed from route I and transferred into route II. It is preferable here to conduct both routes continuously. This particular embodiment of the invention utilizes by-products from route I for further processing in route II. This is particularly economically and ecologically beneficial. There is no disposal of by-products from route I.

The removal of CDEN, CDAN and CDOL and the other high boilers can be undertaken by methods familiar to those skilled in the art. Preference is given here to distillation. More preferably, all removals are effected by means of distillation. It is advantageous to conduct several distillations in succession (multistage distillation).

The CDAN can be distilled off after the epoxidation.

After the rearrangement, it is advantageous first to distil off a mixture of CDAN and CDEN (low boiler fraction) and to subject the residue comprising CDON, CDOL and further high boilers to another distillation. In this case, it is possible to obtain CDON which is separated from a high boiler fraction comprising CDOL. CDOL in turn can be distilled off from the remaining high boiler products.

Low boilers are substances having a boiling point lower than the boiling point of CDON.

FIG. 1 shows a flow diagram with the corresponding reactions. The compounds in italics are by-products of each reaction.

Proceeding from CDT, via route I, CDEN is obtained by means of hydrogenation (selective hydrogenation) and is epoxidized to CDAN epoxide. This is followed by a rearrangement to CDON, with removal of CDEN present—for example by means of distillation—and feeding into the CDEN prior to the epoxidation. The CDEN present after the epoxidation can likewise be recycled. The CDEN recycled may contain CDAN.

The remaining CDON may contain CDOL which can be removed and fed to route II. Alternatively, the CDOL can be dehydrogenated within route I to CDON.

The invention further provides a process for synthesizing laurolactam (lactam process of the invention), in which the aforementioned process of the invention for preparing CDON is employed. In this case, the laurolactam is obtained from CDON, the CDON being prepared by the CDON process of the invention.

The invention further provides a process for synthesising nylon-12 (polyamide process of the invention), in which the aforementioned process of the invention for preparing CDON is employed.

The CDON produced in the CDON process of the invention can be oximated in the lactam or polyamide process of the invention to obtain cyclododecanone oxime (CDON oxime). In the subsequent step, the Beckmann rearrangement may be effected to give laurolactam, in which case the rearrangement can be effected by means of sulphuric acid or cyanuric chloride. The lactam may be subjected to further processing by polycondensation to give polyamide.

The oximation, the Beckmann rearrangement and the condensation reaction are known to a person skilled in the art.

Even in the absence of further information it is assumed that a person skilled in the art can make very extensive use of the above description. The preferred embodiments and examples are therefore to be interpreted merely as descriptive disclosure, and certainly not as disclosure that is in any way limiting.

The present invention is elucidated in detail hereinafter with reference to an example. Alternative embodiments of the present invention are obtainable analogously.

Having generally described this invention, a further understanding can be obtained by reference to certain specific examples which are provided herein for purposes of illustration only, and are not intended to be limiting unless otherwise specified.

EXAMPLES

Unless stated otherwise, the percentage figures are by mass.

Selective Hydrogenation of CDT:

1000 kg/h of CDT were evaporated continuously in a saturation column as gas/liquid contact apparatus at a pressure of 0.75 bar and a temperature of 155° C. into a 10 m$^3$/h cycle gas stream that consisted essentially of nitrogen. The resulting gas stream was fed to a fixed bed reactor having a Pd on $Al_2O_3$ catalyst, in which the reaction with hydrogen was effected at a temperature of 130° C. For this purpose, 25 kg/h of hydrogen were metered into the cycle gas stream at the reactor inlet. At the reactor outlet, the product was condensed out of the cycle gas stream at 35° C. The condensed liquid had a composition of 84.8% CDEN and 15% CDAN. CDDIEN (cyclododecadiene) and CDT isomers were present in concentrations of less than 0.2%.

The remaining cycle gas stream was fed via a compressor back to the saturation column (see above).

Epoxidation of CDEN:

The mixture of CDEN (84.8%) and CDAN (15%) from the selective hydrogenation was epoxidized at a metering rate of 2 kg/h in a three-stage reactor cascade with $H_2O_2$. Additionally recycled into the reactor cascade is a mixture of CDEN (76%) and CDAN (24%) from the low boiler distillation (distillation 1) of the rearrangement step at a metering rate of 80 g/h.

This CDAN/CDEN mixture was first metered continuously into a first 8 l reactor at a metering rate of 2.08 kg/h. Additionally metered into the 5.5 l biphasic reaction mixture at a temperature of 80° C. were a 50% $H_2O_2$ solution (560 g/h), an aqueous solution of 30% by weight of $Na_2WO_4$ and 18% by weight of $H_3PO_4$ (130 g/h), a 50% solution of trioctylamine in CDEN (70 g/h) and water (150 g/h).

The biphasic mixture came from the first reactor with a CDEN conversion of 79% and passed over into a second 8 l reactor. For this purpose, a 50% $H_2O_2$ solution (135 g/h) was metered into the 5.5 l biphasic reaction mixture at a temperature of 78° C.

From this second reactor came a biphasic mixture with a CDEN conversion of 96%, which was passed into a reactor having a fill level of 25 l. The biphasic reaction mixture was stirred in this reactor at a temperature of 76° C.

The two phases of the reaction mixture from the 25 l reactor were separated in a phase separation vessel. The organic phase was subsequently washed with a 5% NaOH solution (0.5 kg/h) in a 5 l vessel and the two phases were separated in a separation vessel.

The organic phase was finally continuously distilled in three stages. In a first column (column with 8 m fabric packing; surface area of 500 m$^2$/m$^3$; top pressure 300 mbar), the residual water was removed into the distillate. The CDAN (320 g/h) was distilled off in a second column (column with 6 m fabric packing; surface area of 500 m$^2$/m$^3$; top pressure 10 mbar), and the CDAN epoxide was collected in the bottoms. In a third column (column with 6 m fabric packing; surface area of 500 m$^2$/m$^3$; top pressure 10 mbar), the desired CDAN epoxide product (purity>99.5%) was obtained in the distillate at a rate of 1.73 kg/h. This corresponds to an overall yield of 98% for the epoxidation.

Rearrangement of CDAN Epoxide to CDON:

The CDAN epoxide from the preceding step was converted to CDON by means of a 0.5% Pd/ZrO$_2$ catalyst in a three-stage reactor cascade.

The CDAN epoxide from the epoxidation was fed into a first circulation reactor at a metering rate of 1.73 kg/h. The circulation reactor consisted of a 12 l tubular reactor which was filled with 10 kg of 0.5% Pd/ZrO$_2$ fixed bed catalyst at a temperature of 220° C. and was fed from an 8 l reservoir vessel.

From the first circulation reactor came a mixture of 65% CDON, 21% CDAN epoxide, 0.9% CDAN, 2.8% CDEN, 2.5% CDOL and 7.8% by-products and intermediates. This mixture was metered into a second circulation reactor at a metering rate of 1.73 kg/h. This second circulation reactor likewise consisted of an 8 l reservoir vessel and a 12 l tubular reactor which was filled with 10 kg of 0.5% Pd/ZrO$_2$ fixed bed catalyst at a temperature of 220° C.

From the second reaction circuit came a mixture comprising 88% CDON, 4% CDAN epoxide, 1.1% CDAN, 3.4% CDEN and 2.9% CDOL. This mixture was metered into a fixed bed reactor filled with 2.7 kg of Pd/ZrO$_2$ at a metering rate of 1.73 kg/h. In this tube, the reaction mixture was heated to a temperature of 230° C. From this tube, a crude mixture with 92% CDON, 1.1% CDAN, 3.5% CDEN and 2.2% CDOL was obtained. The components of this mixture were separated from one another and purified by means of distillation.

Distillation of Low Boiler Fraction:

The crude mixture from the rearrangement was freed of a low boiler fraction (components having a lower boiling point than CDON) in a first continuous distillation step. The column used was equipped with 8 m of fabric packing having a surface area of 500 m$^2$/m$^3$ and was operated at a top pressure of 10 mbar. The distillate (80 g/h) with 76% CDEN and 24% CDAN was recycled into the epoxidation of CDEN (see above). The bottoms were fed into the second distillation column.

Distillation of CDON:

The bottoms from the first distillation were distilled in a further continuous distillation step (column with 6 m fabric packing; surface area of 500 m$^2$/m$^3$), and CDON was obtained as distillate at a top pressure of 10 mbar. Components having a higher boiling point than CDON (for example CDOL) were removed as bottom product. The purity of the CDON obtained was >99% and the CDON yield achieved in the distillation was 98%.

It was possible to convert this cyclododecanone further to laurolactam by known methods.

The bottoms from this second distillation were purified further in an additional column: CDOL was separated from other high boilers in an additional column and was converted to CDON by means of dehydrogenation.

European patent application EP14179454 filed Aug. 1, 2014, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for preparing cyclododecanone (CDON) by a reaction route I, comprising
   a. epoxidizing cyclododecene (CDEN) to epoxycyclododecane (CDAN epoxide), and
   b. rearranging the CDAN epoxide to CDON to obtain a mixture comprising said CDON and CDEN,
   wherein:
   CDEN is separated from the CDON-containing mixture and sent to the epoxidation to CDAN epoxide in step a;
   the CDAN epoxide from step a comprises cyclododecane (CDAN) which is at least partly removed prior to the rearrangement in step b; and
   the CDAN removed prior to the rearrangement in step b is sent to a reaction route II for preparation of CDON, comprising:
   c. hydrogenation of cyclododecatriene (CDT) to CDAN,
   d. oxidation of CDAN to give a mixture comprising cyclododecanol (CDOL) and CDON and
   e. dehydrogenation of CDOL to CDON.

2. The process according to claim 1, wherein CDEN for the epoxidation in step a is obtained from cyclododecatriene (CDT).

3. The process according to claim 1, wherein the rearrangement in step b is effected in the presence of a noble metal catalyst.

4. The process according to claim 3, wherein the catalyst for the rearrangement (step b) comprises titanium dioxide, zirconium dioxide or both.

5. The process according to claim 1, wherein the CDAN epoxide from step a comprises CDEN which is at least partly removed prior to the rearrangement in step b.

6. The process according to claim 1, wherein the CDON-containing mixture comprises cyclododecanol (CDOL) which is dehydrogenated to CDON.

7. The process according to claim 6, wherein the CDOL is separated from the CDON-containing mixture prior to the dehydrogenation and is sent to the reaction route II for preparation of CDON.

8. The process according to claim 1, wherein at least one removal of any compound is conducted by distillation.

9. The process according to claim 1, wherein all removals of any compound are conducted by distillation.

10. The process according to claim 1, wherein CDT is obtained from 1,3-butadiene.

11. A process for synthesizing laurolactam from CDON, wherein the CDON is prepared according to claim 1.

12. The process according to claim 11, wherein the CDON is converted to cyclododecanone oxime (CDON oxime).

13. A process for preparing nylon-12 from CDON, wherein the CDON is prepared according to claim 1.

* * * * *

UNITED STATES PATENT AND TRADEMARK OFFICE
CERTIFICATE OF CORRECTION

PATENT NO. : 9,533,933 B2  
APPLICATION NO. : 14/815014  
DATED : January 3, 2017  
INVENTOR(S) : Kevin Micoine et al.

Page 1 of 1

It is certified that error appears in the above-identified patent and that said Letters Patent is hereby corrected as shown below:

On the Title Page

Item (71), the applicant's information, and Item (72), the inventor's information, are incorrect. Items (71) and (72) should read:

--(71) Applicants: Kevin Micoine, Herten (DE); Ralf Meier, Dortmund (DE); Juergen Herwig, Huenxe (DE); Martin Roos, Haltern am See (DE); Harald Haeger, Luedinghausen (DE); Luca Cameretti, Dortmund (DE); Jens Doering, Dortmund (DE)--

--(72) Inventors: Kevin Micoine, Herten (DE); Ralf Meier, Dortmund (DE); Juergen Herwig, Huenxe (DE); Martin Roos, Haltern am See (DE); Harald Haeger, Luedinghausen (DE); Luca Cameretti, Dortmund (DE); Jens Doering, Dortmund (DE)--

Signed and Sealed this  
Tenth Day of April, 2018

Andrei Iancu  
*Director of the United States Patent and Trademark Office*